(12) United States Patent
Dewitt et al.

(10) Patent No.: US 11,241,339 B2
(45) Date of Patent: *Feb. 8, 2022

(54) PERFORATED BINDER FOR LAMINATED WOUND DRESSING

(71) Applicant: ConvaTec Inc., Las Vegas, NV (US)

(72) Inventors: David Dewitt, Lenoir City, TN (US); Jonathan Veal, Lenoir City, TN (US)

(73) Assignee: CONVATEC INC., Las Vegas, NV (US)

( * ) Notice: Subject to any disclaimer, the term of this patent is extended or adjusted under 35 U.S.C. 154(b) by 433 days.

This patent is subject to a terminal disclaimer.

(21) Appl. No.: 16/261,332

(22) Filed: Jan. 29, 2019

(65) Prior Publication Data

US 2019/0151158 A1    May 23, 2019

Related U.S. Application Data

(63) Continuation of application No. 13/689,133, filed on Nov. 29, 2012, now Pat. No. 10,219,953.

(Continued)

(51) Int. Cl.
*A61F 13/00* (2006.01)
*A61F 13/02* (2006.01)

(52) U.S. Cl.
CPC .... *A61F 13/0206* (2013.01); *A61F 13/00063* (2013.01); *A61F 13/0203* (2013.01);

(Continued)

(58) Field of Classification Search
CPC .. A61F 2013/00246; A61F 2013/00604; A61F 2013/00634; A61F 2013/0091;
(Continued)

(56) References Cited

U.S. PATENT DOCUMENTS 5,681,579 A * 10/1997 Freeman ............... A61F 13/023
424/448
6,649,011 B1 * 11/2003 Hardt ................... A61K 9/7023
156/267

(Continued)

FOREIGN PATENT DOCUMENTS

EP    3187204 A1    7/2017
EP    3643328 A1    4/2020
(Continued)

*Primary Examiner* — Kim M Lewis
(74) *Attorney, Agent, or Firm* — Taft Stettinius & Hollister LLP; Ryan O. White; Derek B. Lavender

(57) ABSTRACT

A binder layer for a laminated wound dressing is brought into contact with a sheet coated with a pattern-coated adhesive sheet. As the binder layer is in contact with the pattern-coated adhesive sheet, a series of closed-loop cuts are made in the binder layer. The closed-loop cuts are made in such a way that the material enclosed by each closed loop is substantially physically separated from the remainder of the binder layer. Then the binder layer is moved away from the pattern-coated adhesive sheet, so that the binder layer and the pattern-coated adhesive sheet are no longer in contact. When the binder layer and the pattern-coated adhesive sheet are moved apart, the material enclosed in the closed-loop cuts—i.e., the cut waste fragments—are retained on the pattern-coated adhesive sheet, ensuring that the binder layer includes a series of cleared perforations.

15 Claims, 3 Drawing Sheets

Related U.S. Application Data

(60) Provisional application No. 61/564,612, filed on Nov. 29, 2011.

(52) U.S. Cl.
CPC ........ *A61F 13/025* (2013.01); *A61F 13/0276* (2013.01); *A61F 2013/0091* (2013.01); *A61F 2013/00246* (2013.01); *A61F 2013/00604* (2013.01); *A61F 2013/00634* (2013.01); *A61F 2013/00936* (2013.01)

(58) Field of Classification Search
CPC .. A61F 2013/00936; A61F 2013/00225; A61F 2013/00229; A61F 2013/00548; A61F 2013/00421; A61L 31/048; A61L 2300/00; A61L 31/10; A61L 31/146; A61L 31/16

See application file for complete search history.

(56) References Cited

U.S. PATENT DOCUMENTS

| | | | |
|---|---|---|---|
| 6,953,602 B2 * | 10/2005 | Carte | A61F 13/023 427/208.4 |
| 10,016,537 B2 | 7/2018 | Menon et al. | |
| 10,046,096 B2 | 8/2018 | Askem et al. | |
| 10,076,447 B2 | 9/2018 | Barta et al. | |
| 10,076,587 B2 | 9/2018 | Locke et al. | |
| 10,143,784 B2 | 12/2018 | Walton et al. | |
| 10,426,670 B2 | 10/2019 | van Blucher et al. | |
| 10,426,747 B2 | 10/2019 | Johnson | |
| 10,426,874 B2 | 10/2019 | Chien et al. | |
| 10,426,875 B2 | 10/2019 | Blott et al. | |
| 10,426,938 B2 | 10/2019 | Locke et al. | |
| 10,434,015 B2 | 10/2019 | Taylor et al. | |
| 10,434,142 B2 | 10/2019 | Niazi et al. | |
| 10,434,210 B2 | 10/2019 | Olson et al. | |
| 10,434,284 B2 | 10/2019 | Hanson et al. | |
| 10,449,094 B2 | 10/2019 | Donda et al. | |
| D866,756 S | 11/2019 | Allen et al. | |
| 10,463,760 B2 | 11/2019 | Karthikeyan et al. | |
| 10,463,773 B2 | 11/2019 | Haggstrom et al. | |
| 10,470,933 B2 | 11/2019 | Riesinger | |
| 10,470,936 B2 | 11/2019 | Wohlgemuth et al. | |
| 10,471,122 B2 | 11/2019 | Shi et al. | |
| 10,471,190 B2 | 11/2019 | Locke et al. | |
| 10,478,345 B2 | 11/2019 | Barta et al. | |
| 10,478,346 B2 | 11/2019 | Knutson | |
| 10,478,394 B2 | 11/2019 | Yu | |
| 10,485,707 B2 | 11/2019 | Sexton | |
| 10,485,891 B2 | 11/2019 | Andrews et al. | |
| 10,485,892 B2 | 11/2019 | Hands et al. | |
| 10,485,906 B2 | 11/2019 | Freedman et al. | |
| 10,486,135 B2 | 11/2019 | Yang et al. | |
| 10,492,956 B2 | 12/2019 | Zamierowski | |
| 10,493,178 B2 | 12/2019 | Marchant et al. | |
| 10,493,184 B2 | 12/2019 | Collinson et al. | |
| 10,493,185 B2 | 12/2019 | Stokes et al. | |
| 10,500,099 B2 | 12/2019 | Hung et al. | |
| 10,500,103 B2 | 12/2019 | Croizat et al. | |
| 10,500,104 B2 | 12/2019 | Sookraj | |
| 10,500,173 B2 | 12/2019 | Yang et al. | |
| 10,500,235 B2 | 12/2019 | Wardell | |
| 10,500,300 B2 | 12/2019 | Dybe et al. | |
| 10,500,301 B2 | 12/2019 | Laurensou | |
| 10,500,302 B2 | 12/2019 | Holm et al. | |
| 10,501,487 B2 | 12/2019 | Andrews et al. | |
| 10,506,928 B2 | 12/2019 | Locke et al. | |
| 10,507,141 B2 | 12/2019 | Allen et al. | |
| 10,507,259 B2 | 12/2019 | Cree et al. | |
| 10,512,707 B2 | 12/2019 | Whalen, III et al. | |
| 10,525,170 B2 | 1/2020 | Havenstrite et al. | |
| 10,532,137 B2 | 1/2020 | Pratt et al. | |
| 10,532,194 B2 | 1/2020 | Locke et al. | |
| 10,537,657 B2 | 1/2020 | Phillips et al. | |
| 10,542,936 B2 | 1/2020 | Goldberg et al. | |
| 10,543,133 B2 | 1/2020 | Shaw et al. | |
| 10,543,293 B2 | 1/2020 | Suschek | |
| 10,548,777 B2 | 2/2020 | Locke et al. | |
| 10,549,008 B2 | 2/2020 | Yoo | |
| 10,549,016 B2 | 2/2020 | Bushko et al. | |
| 10,549,017 B2 | 2/2020 | Hsiao et al. | |
| 10,555,838 B2 | 2/2020 | Wu et al. | |
| 10,555,839 B2 | 2/2020 | Hartwell | |
| 10,556,044 B2 | 2/2020 | Robinson et al. | |
| 10,561,533 B2 | 2/2020 | Hoggarth et al. | |
| 10,561,536 B2 | 2/2020 | Holm et al. | |
| 10,568,767 B2 | 2/2020 | Addison et al. | |
| 10,568,768 B2 | 2/2020 | Long et al. | |
| 10,568,770 B2 | 2/2020 | Robinson et al. | |
| 10,568,771 B2 | 2/2020 | MacDonald et al. | |
| 10,568,773 B2 | 2/2020 | Tuck et al. | |
| 10,568,983 B2 | 2/2020 | Gerdes et al. | |
| 10,575,991 B2 | 3/2020 | Dunn | |
| 10,575,992 B2 | 3/2020 | Sarangapani et al. | |
| 10,576,037 B2 | 3/2020 | Harrell | |
| 10,576,189 B2 | 3/2020 | Locke et al. | |
| 10,583,042 B2 | 3/2020 | Sarangapani et al. | |
| 10,583,228 B2 | 3/2020 | Shuler et al. | |
| 10,589,007 B2 | 3/2020 | Coulthard et al. | |
| 10,590,184 B2 | 3/2020 | Kuo | |
| 10,610,414 B2 | 4/2020 | Hartwell et al. | |
| 10,610,415 B2 | 4/2020 | Griffey et al. | |
| 10,610,623 B2 | 4/2020 | Robinson et al. | |
| 10,617,569 B2 | 4/2020 | Bonn | |
| 10,617,608 B2 | 4/2020 | Shin et al. | |
| 10,617,769 B2 | 4/2020 | Huang | |
| 10,617,784 B2 | 4/2020 | Yu et al. | |
| 10,617,786 B2 | 4/2020 | Kluge et al. | |
| 10,618,266 B2 | 4/2020 | Wright et al. | |
| 10,624,984 B2 | 4/2020 | Courage et al. | |
| 10,625,002 B2 | 4/2020 | Locke et al. | |
| 10,632,019 B2 | 4/2020 | Vitaris | |
| 10,632,224 B2 | 4/2020 | Hardy et al. | |
| 10,639,206 B2 | 5/2020 | Hu et al. | |
| 10,639,350 B2 | 5/2020 | Arber et al. | |
| 10,639,404 B2 | 5/2020 | Lichtenstein | |
| 10,646,614 B2 | 5/2020 | Grinstaff et al. | |
| 10,653,562 B2 | 5/2020 | Robinson et al. | |
| 10,653,782 B2 | 5/2020 | Ameer et al. | |
| 10,653,810 B2 | 5/2020 | Datt et al. | |
| 10,653,821 B2 | 5/2020 | Nichols | |
| 10,653,823 B2 | 5/2020 | Bharti et al. | |
| 10,660,799 B2 | 5/2020 | Wu et al. | |
| 10,660,851 B2 | 5/2020 | Millis et al. | |
| 10,660,992 B2 | 5/2020 | Canner et al. | |
| 10,660,994 B2 | 5/2020 | Askem et al. | |
| 10,667,955 B2 | 6/2020 | Allen et al. | |
| 10,667,956 B2 | 6/2020 | Van Holten et al. | |
| 10,682,257 B2 | 6/2020 | Lu | |
| 10,682,258 B2 | 6/2020 | Manwaring et al. | |
| 10,682,259 B2 | 6/2020 | Hunt et al. | |
| 10,682,318 B2 | 6/2020 | Twomey et al. | |
| 10,682,386 B2 | 6/2020 | Ellis-Behnke et al. | |
| 10,682,446 B2 | 6/2020 | Askem et al. | |
| 10,687,983 B2 | 6/2020 | Dahlberg et al. | |
| 10,687,985 B2 | 6/2020 | Lee et al. | |
| 10,688,215 B2 | 6/2020 | Munro et al. | |
| 10,688,217 B2 | 6/2020 | Hanson et al. | |
| RE48,117 E | 7/2020 | Albert et al. | |
| 10,702,419 B2 | 7/2020 | Locke et al. | |
| 10,702,420 B2 | 7/2020 | Hammond et al. | |
| 10,703,942 B2 | 7/2020 | Tunius | |
| 10,709,760 B2 | 7/2020 | Gronberg et al. | |
| 10,709,807 B2 | 7/2020 | Kshirsagar | |
| 10,709,883 B2 | 7/2020 | Spector | |
| 10,716,711 B2 | 7/2020 | Locke et al. | |
| 10,716,874 B2 | 7/2020 | Koyama et al. | |
| 10,729,589 B2 | 8/2020 | Dorian et al. | |
| 10,729,590 B2 | 8/2020 | Simmons et al. | |
| 10,729,826 B2 | 8/2020 | Lin | |
| 10,736,787 B2 | 8/2020 | Hannigan et al. | |
| 10,736,788 B2 | 8/2020 | Locke et al. | |

(56) References Cited

U.S. PATENT DOCUMENTS

| | | |
|---|---|---|
| 10,736,985 B2 | 8/2020 | Odermatt et al. |
| 10,737,003 B2 | 8/2020 | Fujisaki |
| 10,743,900 B2 | 8/2020 | Ingram et al. |
| 10,744,040 B2 | 8/2020 | Kazala, Jr. et al. |
| 10,744,041 B2 | 8/2020 | Hartwell |
| 10,744,225 B2 | 8/2020 | Lindgren et al. |
| 10,744,237 B2 | 8/2020 | Guidi et al. |
| 10,744,238 B2 | 8/2020 | Guidi et al. |
| 10,744,239 B2 | 8/2020 | Armstrong et al. |
| 10,744,240 B2 | 8/2020 | Simmons et al. |
| 10,751,212 B2 | 8/2020 | Raza et al. |
| 10,751,442 B2 | 8/2020 | Bonnefin et al. |
| 10,751,452 B2 | 8/2020 | Topaz |
| 10,758,423 B2 | 9/2020 | Pigg et al. |
| 10,758,424 B2 | 9/2020 | Blott et al. |
| 10,758,425 B2 | 9/2020 | Blott et al. |
| 10,758,426 B2 | 9/2020 | Eddy |
| 10,758,651 B2 | 9/2020 | Blott et al. |
| 10,765,561 B2 | 9/2020 | Lattimore et al. |
| 10,765,783 B2 | 9/2020 | Locke et al. |
| 10,772,767 B2 | 9/2020 | Bjork et al. |
| 10,772,999 B2 | 9/2020 | Svensby |
| 10,779,993 B2 | 9/2020 | Bishop et al. |
| 10,780,114 B2 | 9/2020 | Udagawa et al. |
| 10,780,194 B2 | 9/2020 | Flach et al. |
| 10,780,201 B2 | 9/2020 | Lin |
| 10,780,202 B2 | 9/2020 | Askem et al. |
| 10,780,203 B2 | 9/2020 | Coulthard et al. |
| 10,782,238 B2 | 9/2020 | Hicks et al. |
| 10,792,191 B2 | 10/2020 | Robinson et al. |
| 10,792,192 B2 | 10/2020 | Tout et al. |
| 10,792,337 B2 | 10/2020 | Leung et al. |
| 10,792,404 B2 | 10/2020 | Hu et al. |
| 10,792,482 B2 | 10/2020 | Randolph et al. |
| 10,800,905 B2 | 10/2020 | Delli-Santi et al. |
| 10,806,819 B2 | 10/2020 | Shuler |
| 2006/0155260 A1 | 7/2006 | Blott et al. |
| 2006/0172000 A1 | 8/2006 | Cullen et al. |
| 2007/0141130 A1* | 6/2007 | Villanueva ............... A61L 15/46 424/445 |
| 2007/0185426 A1 | 8/2007 | Ambrosio et al. |
| 2007/0219512 A1 | 9/2007 | Heaton et al. |
| 2007/0239078 A1 | 10/2007 | Jaeb |
| 2009/0234307 A1 | 9/2009 | Vitaris |
| 2009/0259203 A1 | 10/2009 | Hu et al. |
| 2009/0293887 A1 | 12/2009 | Wilkes et al. |
| 2009/0299303 A1 | 12/2009 | Seegert |
| 2010/0015208 A1 | 1/2010 | Kershaw et al. |
| 2010/0030178 A1 | 2/2010 | MacMeccan et al. |
| 2010/0125233 A1 | 5/2010 | Edward et al. |
| 2010/0125258 A1 | 5/2010 | Coulthard et al. |
| 2010/0137775 A1 | 6/2010 | Hu et al. |
| 2010/0185163 A1 | 7/2010 | Heagle |
| 2010/0298790 A1 | 11/2010 | Guidi et al. |
| 2011/0015595 A1 | 1/2011 | Robinson et al. |
| 2011/0028918 A1 | 2/2011 | Hartwell |
| 2011/0112457 A1 | 5/2011 | Holm et al. |
| 2011/0178451 A1 | 7/2011 | Robinson et al. |
| 2011/0224593 A1 | 9/2011 | Tunius |
| 2011/0224630 A1 | 9/2011 | Simmons et al. |
| 2011/0230849 A1 | 9/2011 | Coulthard et al. |
| 2011/0251566 A1 | 10/2011 | Zimnitsky et al. |
| 2011/0257572 A1 | 10/2011 | Locke et al. |
| 2011/0257573 A1 | 10/2011 | Hong et al. |
| 2011/0275972 A1 | 11/2011 | Rosenberg |
| 2012/0071845 A1 | 3/2012 | Hu et al. |
| 2012/0089068 A1* | 4/2012 | McClure, Jr. ...... A61F 13/00029 602/48 |
| 2012/0130332 A1 | 5/2012 | Cotton et al. |
| 2012/0136325 A1 | 5/2012 | Allen et al. |
| 2012/0209226 A1 | 8/2012 | Simmons et al. |
| 2013/0053795 A1 | 2/2013 | Coulthard et al. |
| 2013/0123728 A1 | 5/2013 | Pratt et al. |
| 2013/0226063 A1 | 8/2013 | Taylor et al. |
| 2014/0005618 A1 | 1/2014 | Locke et al. |
| 2014/0074053 A1 | 3/2014 | Locke et al. |
| 2014/0188060 A1 | 7/2014 | Robinson et al. |
| 2014/0194838 A1 | 7/2014 | Wibaux et al. |
| 2014/0200532 A1 | 7/2014 | Robinson et al. |
| 2014/0236112 A1 | 8/2014 | Von Wolff et al. |
| 2014/0256925 A1 | 9/2014 | Catchmark et al. |
| 2014/0276499 A1 | 9/2014 | Locke et al. |
| 2014/0296804 A1 | 10/2014 | Hicks et al. |
| 2014/0308338 A1 | 10/2014 | Nierle et al. |
| 2014/0309574 A1 | 10/2014 | Cotton |
| 2015/0018433 A1 | 1/2015 | Leipzig et al. |
| 2015/0057624 A1 | 2/2015 | Simmons et al. |
| 2015/0071985 A1 | 3/2015 | Walker et al. |
| 2015/0079152 A1 | 3/2015 | Wuollett et al. |
| 2015/0094674 A1 | 4/2015 | Pratt et al. |
| 2015/0104486 A1 | 4/2015 | Bonnefin et al. |
| 2015/0112311 A1 | 4/2015 | Hammond et al. |
| 2015/0119831 A1 | 4/2015 | Robinson et al. |
| 2015/0119834 A1 | 4/2015 | Locke et al. |
| 2015/0141941 A1 | 5/2015 | Allen et al. |
| 2015/0148785 A1 | 5/2015 | Kleiner |
| 2015/0174304 A1 | 6/2015 | Askem et al. |
| 2015/0245949 A1 | 9/2015 | Locke et al. |
| 2015/0246164 A1 | 9/2015 | Heaton et al. |
| 2015/0250979 A1 | 9/2015 | Loske |
| 2015/0265741 A1 | 9/2015 | Duncan et al. |
| 2015/0265743 A1 | 9/2015 | Hanson et al. |
| 2015/0320901 A1 | 11/2015 | Chandrashekhar-Bhat et al. |
| 2016/0008293 A1 | 1/2016 | Shi et al. |
| 2016/0038626 A1 | 2/2016 | Locke et al. |
| 2016/0051724 A1 | 2/2016 | Sahin et al. |
| 2016/0067107 A1 | 3/2016 | Cotton |
| 2016/0100987 A1 | 4/2016 | Hartwell et al. |
| 2016/0106878 A1 | 4/2016 | Yang et al. |
| 2016/0106892 A1 | 4/2016 | Hartwell |
| 2016/0166422 A1 | 6/2016 | Karim et al. |
| 2016/0193244 A1 | 7/2016 | Ota et al. |
| 2016/0222548 A1 | 8/2016 | Agboh |
| 2016/0271178 A1 | 9/2016 | Hauser et al. |
| 2016/0287743 A1 | 10/2016 | Andrews |
| 2016/0339158 A1 | 11/2016 | Collinson et al. |
| 2016/0374847 A1 | 12/2016 | Lachenbruch et al. |
| 2017/0014275 A1 | 1/2017 | Schneider |
| 2017/0049111 A1 | 2/2017 | Patton et al. |
| 2017/0072669 A1 | 3/2017 | Sekido et al. |
| 2017/0128269 A1 | 5/2017 | Coulthard et al. |
| 2017/0189237 A1 | 7/2017 | Locke et al. |
| 2017/0189575 A1 | 7/2017 | Lee et al. |
| 2017/0209615 A1 | 7/2017 | Tornero Garcia et al. |
| 2017/0232161 A1 | 8/2017 | Fewkes et al. |
| 2017/0258956 A1 | 9/2017 | Flach et al. |
| 2017/0367895 A1 | 12/2017 | Holm et al. |
| 2017/0368239 A1 | 12/2017 | Askem et al. |
| 2018/0008742 A1 | 1/2018 | Hoggarth et al. |
| 2018/0014974 A1 | 1/2018 | Hoggarth et al. |
| 2018/0023217 A1 | 1/2018 | Patton et al. |
| 2018/0030321 A1 | 2/2018 | Tunius |
| 2018/0042789 A1 | 2/2018 | Bradford et al. |
| 2018/0078423 A1 | 3/2018 | Magin et al. |
| 2018/0086903 A1 | 3/2018 | Zhang et al. |
| 2018/0118809 A1 | 5/2018 | Mearns Spragg |
| 2018/0133066 A1 | 5/2018 | Ahsani et al. |
| 2018/0140467 A1 | 5/2018 | Hunt |
| 2018/0140822 A1 | 5/2018 | Robinson et al. |
| 2018/0200414 A1 | 7/2018 | Askem et al. |
| 2018/0221531 A1 | 8/2018 | Bender et al. |
| 2018/0236124 A1 | 8/2018 | Young et al. |
| 2018/0243463 A1 | 8/2018 | Chatterjee et al. |
| 2018/0243464 A1 | 8/2018 | Hwang et al. |
| 2018/0244857 A1 | 8/2018 | Lee et al. |
| 2018/0272052 A1 | 9/2018 | Locke et al. |
| 2018/0296397 A1 | 10/2018 | Askem et al. |
| 2018/0303873 A1 | 10/2018 | Been et al. |
| 2018/0311419 A1 | 11/2018 | Locke et al. |
| 2018/0333522 A1 | 11/2018 | Pratt et al. |
| 2018/0344533 A1 | 12/2018 | Rovaniemi |
| 2018/0353334 A1 | 12/2018 | Locke et al. |
| 2018/0353337 A1 | 12/2018 | Locke |
| 2018/0353339 A1 | 12/2018 | Locke et al. |

(56) References Cited

U.S. PATENT DOCUMENTS

| | | |
|---|---|---|
| 2018/0353340 A1 | 12/2018 | Robinson et al. |
| 2018/0353344 A1 | 12/2018 | Locke et al. |
| 2018/0353662 A1 | 12/2018 | Locke et al. |
| 2018/0353663 A1 | 12/2018 | Locke et al. |
| 2018/0360667 A1 | 12/2018 | Droche |
| 2019/0000677 A1 | 1/2019 | Munro |
| 2019/0015258 A1 | 1/2019 | Gowans et al. |
| 2019/0015468 A1 | 1/2019 | Yadav et al. |
| 2019/0030223 A1 | 1/2019 | Lin |
| 2019/0046682 A1 | 2/2019 | Choi et al. |
| 2019/0060127 A1 | 2/2019 | Locke et al. |
| 2019/0083752 A1 | 3/2019 | Howell et al. |
| 2019/0117465 A1 | 4/2019 | Osborne et al. |
| 2019/0117466 A1 | 4/2019 | Kazala, Jr. et al. |
| 2019/0117861 A1 | 4/2019 | Locke et al. |
| 2019/0125590 A1 | 5/2019 | Rehbein et al. |
| 2019/0133830 A1 | 5/2019 | Bishop et al. |
| 2019/0151155 A1 | 5/2019 | Bonn |
| 2019/0151159 A1 | 5/2019 | Gowans et al. |
| 2019/0151495 A1 | 5/2019 | Helary et al. |
| 2019/0184052 A1 | 6/2019 | Ilan et al. |
| 2019/0231600 A1 | 8/2019 | Locke et al. |
| 2019/0231602 A1 | 8/2019 | Locke et al. |
| 2019/0231943 A1 | 8/2019 | Robinson et al. |
| 2019/0274889 A1 | 9/2019 | Steward et al. |
| 2019/0282728 A1 | 9/2019 | Kellar et al. |
| 2019/0290799 A1 | 9/2019 | Arshi et al. |
| 2019/0298249 A1 | 10/2019 | Bates et al. |
| 2019/0298577 A1 | 10/2019 | Locke et al. |
| 2019/0298578 A1 | 10/2019 | Shulman et al. |
| 2019/0298579 A1 | 10/2019 | Moore et al. |
| 2019/0298580 A1 | 10/2019 | Hall et al. |
| 2019/0298582 A1 | 10/2019 | Addison et al. |
| 2019/0298881 A1 | 10/2019 | Ramjit et al. |
| 2019/0298882 A1 | 10/2019 | Nelson |
| 2019/0298895 A1 | 10/2019 | Selby et al. |
| 2019/0307611 A1 | 10/2019 | Askem et al. |
| 2019/0307612 A1 | 10/2019 | Hartwell et al. |
| 2019/0307934 A1 | 10/2019 | Allen et al. |
| 2019/0307935 A1 | 10/2019 | Simmons et al. |
| 2019/0314187 A1 | 10/2019 | Emslander et al. |
| 2019/0314209 A1 | 10/2019 | Ha et al. |
| 2019/0314544 A1 | 10/2019 | Filho et al. |
| 2019/0321232 A1 | 10/2019 | Jardret et al. |
| 2019/0321509 A1 | 10/2019 | Chakravarthy et al. |
| 2019/0321526 A1 | 10/2019 | Robinson et al. |
| 2019/0322795 A1 | 10/2019 | Kubo et al. |
| 2019/0328580 A1 | 10/2019 | Emslander et al. |
| 2019/0336343 A1 | 11/2019 | Etchells et al. |
| 2019/0336344 A1 | 11/2019 | Locke |
| 2019/0336345 A1 | 11/2019 | Bannwart |
| 2019/0336346 A1 | 11/2019 | Locke et al. |
| 2019/0336640 A1 | 11/2019 | Vismara et al. |
| 2019/0336641 A1 | 11/2019 | Nisbet |
| 2019/0336643 A1 | 11/2019 | Luukko et al. |
| 2019/0336658 A1 | 11/2019 | Heaton et al. |
| 2019/0336739 A1 | 11/2019 | Locke et al. |
| 2019/0343687 A1 | 11/2019 | Locke et al. |
| 2019/0343889 A1 | 11/2019 | Luukko et al. |
| 2019/0343979 A1 | 11/2019 | Kearney et al. |
| 2019/0343993 A1 | 11/2019 | Weston |
| 2019/0343994 A1 | 11/2019 | Greener |
| 2019/0344242 A1 | 11/2019 | Kim et al. |
| 2019/0350763 A1 | 11/2019 | Pratt et al. |
| 2019/0350764 A1 | 11/2019 | Zochowski et al. |
| 2019/0350765 A1 | 11/2019 | Heagle et al. |
| 2019/0350775 A1 | 11/2019 | Biasutti et al. |
| 2019/0350970 A1 | 11/2019 | Saphier et al. |
| 2019/0351092 A1 | 11/2019 | Silver et al. |
| 2019/0351093 A1 | 11/2019 | Stein et al. |
| 2019/0351094 A1 | 11/2019 | Maher et al. |
| 2019/0351095 A1 | 11/2019 | Maher et al. |
| 2019/0351111 A1 | 11/2019 | Locke et al. |
| 2019/0358088 A1 | 11/2019 | Lavocah et al. |
| 2019/0358361 A1 | 11/2019 | McInnes et al. |
| 2019/0358372 A1 | 11/2019 | Askem et al. |
| 2019/0365948 A1 | 12/2019 | Deegan et al. |
| 2019/0365962 A1 | 12/2019 | Lee et al. |
| 2019/0374408 A1 | 12/2019 | Robles et al. |
| 2019/0374673 A1 | 12/2019 | Hoefinghoff et al. |
| 2019/0380878 A1 | 12/2019 | Edwards et al. |
| 2019/0380881 A1 | 12/2019 | Albert et al. |
| 2019/0380882 A1 | 12/2019 | Taylor et al. |
| 2019/0380883 A1 | 12/2019 | Macphee et al. |
| 2019/0381222 A9 | 12/2019 | Locke et al. |
| 2019/0388577 A1 | 12/2019 | Chandrashekhar-Bhat et al. |
| 2019/0388579 A1 | 12/2019 | Macphee et al. |
| 2019/0388589 A1 | 12/2019 | Macphee et al. |
| 2020/0000640 A1 | 1/2020 | Mondal et al. |
| 2020/0000642 A1 | 1/2020 | Waite |
| 2020/0000643 A1 | 1/2020 | Locke |
| 2020/0000955 A1 | 1/2020 | Andrews et al. |
| 2020/0000956 A1 | 1/2020 | Huang et al. |
| 2020/0000960 A1 | 1/2020 | Kellar et al. |
| 2020/0000985 A1 | 1/2020 | Seddon et al. |
| 2020/0008981 A1 | 1/2020 | Wheldrake |
| 2020/0009289 A1 | 1/2020 | Torabinejad et al. |
| 2020/0009400 A1 | 1/2020 | Ribeiro et al. |
| 2020/0017650 A1 | 1/2020 | Young et al. |
| 2020/0022844 A1 | 1/2020 | Blott et al. |
| 2020/0023102 A1 | 1/2020 | Powell |
| 2020/0023103 A1 | 1/2020 | Joshi et al. |
| 2020/0023104 A1 | 1/2020 | Eriksson et al. |
| 2020/0023105 A1 | 1/2020 | Long et al. |
| 2020/0023106 A1 | 1/2020 | Carroll et al. |
| 2020/0030153 A1 | 1/2020 | Johannison et al. |
| 2020/0030480 A1 | 1/2020 | Choi |
| 2020/0030499 A1 | 1/2020 | Menon et al. |
| 2020/0038023 A1 | 2/2020 | Dunn |
| 2020/0038249 A1 | 2/2020 | Pratt et al. |
| 2020/0038250 A1 | 2/2020 | Edwards et al. |
| 2020/0038251 A1 | 2/2020 | Locke et al. |
| 2020/0038252 A1 | 2/2020 | Spiro |
| 2020/0038283 A1 | 2/2020 | Hall et al. |
| 2020/0038470 A1 | 2/2020 | Datt et al. |
| 2020/0038544 A1 | 2/2020 | Grover et al. |
| 2020/0038546 A1 | 2/2020 | Dizio et al. |
| 2020/0038639 A1 | 2/2020 | Patel et al. |
| 2020/0046565 A1 | 2/2020 | Barta et al. |
| 2020/0046566 A1 | 2/2020 | Carey et al. |
| 2020/0046567 A1 | 2/2020 | Carroll et al. |
| 2020/0046568 A1 | 2/2020 | Sexton |
| 2020/0046663 A1 | 2/2020 | Murdock et al. |
| 2020/0046876 A1 | 2/2020 | Liu |
| 2020/0046887 A1 | 2/2020 | Runquist et al. |
| 2020/0054491 A1 | 2/2020 | Hentrich et al. |
| 2020/0054781 A1 | 2/2020 | Weiser et al. |
| 2020/0060879 A1 | 2/2020 | Edwards et al. |
| 2020/0061253 A1 | 2/2020 | Long et al. |
| 2020/0061254 A1 | 2/2020 | Joshi et al. |
| 2020/0061379 A1 | 2/2020 | Bogie et al. |
| 2020/0069183 A1 | 3/2020 | Rice et al. |
| 2020/0069476 A1 | 3/2020 | Randolph et al. |
| 2020/0069477 A1 | 3/2020 | Holm et al. |
| 2020/0069478 A1 | 3/2020 | Jabbarzadeh et al. |
| 2020/0069479 A1 | 3/2020 | Buan et al. |
| 2020/0069835 A1 | 3/2020 | Hissink et al. |
| 2020/0069850 A1 | 3/2020 | Beadle et al. |
| 2020/0069851 A1 | 3/2020 | Blott et al. |
| 2020/0069853 A1 | 3/2020 | Hall et al. |
| 2020/0078223 A1 | 3/2020 | Locke et al. |
| 2020/0078224 A1 | 3/2020 | Carroll et al. |
| 2020/0078225 A1 | 3/2020 | Grillitsch et al. |
| 2020/0078305 A1 | 3/2020 | Auvinen et al. |
| 2020/0078330 A1 | 3/2020 | Gay |
| 2020/0078482 A1 | 3/2020 | Yoon et al. |
| 2020/0078499 A1 | 3/2020 | Gadde et al. |
| 2020/0085625 A1 | 3/2020 | Bellini et al. |
| 2020/0085626 A1 | 3/2020 | Braga et al. |
| 2020/0085629 A1 | 3/2020 | Locke et al. |
| 2020/0085630 A1 | 3/2020 | Robinson et al. |
| 2020/0085632 A1 | 3/2020 | Locke et al. |
| 2020/0085991 A1 | 3/2020 | Coomber |
| 2020/0085992 A1 | 3/2020 | Locke et al. |

(56) References Cited

U.S. PATENT DOCUMENTS

| | | |
|---|---|---|
| 2020/0086014 A1 | 3/2020 | Locke et al. |
| 2020/0086017 A1 | 3/2020 | Jardret et al. |
| 2020/0086049 A1 | 3/2020 | Park et al. |
| 2020/0093646 A1 | 3/2020 | Locke et al. |
| 2020/0093756 A1 | 3/2020 | Sabacinski |
| 2020/0093953 A1 | 3/2020 | Kim et al. |
| 2020/0093954 A1 | 3/2020 | Leise, III |
| 2020/0093970 A1 | 3/2020 | Hunt et al. |
| 2020/0095421 A1 | 3/2020 | Kettel |
| 2020/0100945 A1 | 4/2020 | Albert et al. |
| 2020/0101192 A1 | 4/2020 | Folwarzny |
| 2020/0107964 A1 | 4/2020 | Locke et al. |
| 2020/0107965 A1 | 4/2020 | Greener |
| 2020/0107966 A1 | 4/2020 | Francis |
| 2020/0107967 A1 | 4/2020 | Holm et al. |
| 2020/0108169 A1 | 4/2020 | Hu et al. |
| 2020/0113741 A1 | 4/2020 | Rehbein et al. |
| 2020/0114039 A1 | 4/2020 | Wang et al. |
| 2020/0114040 A1 | 4/2020 | Waite et al. |
| 2020/0114049 A1 | 4/2020 | Wall |
| 2020/0121509 A1 | 4/2020 | Locke et al. |
| 2020/0121510 A1 | 4/2020 | Hartwell et al. |
| 2020/0121513 A1 | 4/2020 | Townsend et al. |
| 2020/0121521 A1 | 4/2020 | Daniel et al. |
| 2020/0121833 A9 | 4/2020 | Askem et al. |
| 2020/0129338 A1 | 4/2020 | Gardiner et al. |
| 2020/0129341 A1 | 4/2020 | Coulthard et al. |
| 2020/0129648 A1 | 4/2020 | Drury et al. |
| 2020/0129654 A1 | 4/2020 | Bouvier et al. |
| 2020/0129655 A1 | 4/2020 | Gardiner et al. |
| 2020/0129675 A1 | 4/2020 | Robinson et al. |
| 2020/0138754 A1 | 5/2020 | Johnson |
| 2020/0139002 A1 | 5/2020 | Dudnyk et al. |
| 2020/0139023 A1 | 5/2020 | Haggstrom et al. |
| 2020/0139025 A1 | 5/2020 | Robinson et al. |
| 2020/0141031 A1 | 5/2020 | Kosan et al. |
| 2020/0146894 A1 | 5/2020 | Long et al. |
| 2020/0146896 A1 | 5/2020 | Rice et al. |
| 2020/0146897 A1 | 5/2020 | Locke et al. |
| 2020/0146899 A1 | 5/2020 | Pratt et al. |
| 2020/0155355 A1 | 5/2020 | Hill et al. |
| 2020/0155358 A1 | 5/2020 | Wheldrake |
| 2020/0155359 A1 | 5/2020 | Carroll et al. |
| 2020/0155361 A1 | 5/2020 | Pigg et al. |
| 2020/0155379 A1 | 5/2020 | Shaw et al. |
| 2020/0163802 A1 | 5/2020 | Hunt et al. |
| 2020/0163803 A1 | 5/2020 | Pigg et al. |
| 2020/0164112 A1 | 5/2020 | Kato et al. |
| 2020/0164120 A1 | 5/2020 | Jaecklein et al. |
| 2020/0170841 A1 | 6/2020 | Waite et al. |
| 2020/0170842 A1 | 6/2020 | Locke |
| 2020/0170843 A1 | 6/2020 | Collinson et al. |
| 2020/0171197 A1 | 6/2020 | Hubbell et al. |
| 2020/0179300 A1 | 6/2020 | Urban et al. |
| 2020/0179558 A1 | 6/2020 | Munro et al. |
| 2020/0179673 A1 | 6/2020 | Wan |
| 2020/0188179 A1 | 6/2020 | Bugedo-Albizur et al. |
| 2020/0188180 A1 | 6/2020 | Akbari et al. |
| 2020/0188182 A1 | 6/2020 | Sanders et al. |
| 2020/0188183 A1 | 6/2020 | Hamerslagh et al. |
| 2020/0188550 A1 | 6/2020 | Dagger et al. |
| 2020/0188564 A1 | 6/2020 | Dunn |
| 2020/0190310 A1 | 6/2020 | Meyer |
| 2020/0197227 A1 | 6/2020 | Locke et al. |
| 2020/0197228 A1 | 6/2020 | Hartwell |
| 2020/0197559 A1 | 6/2020 | Bourdillon et al. |
| 2020/0197580 A1 | 6/2020 | Kilpadi et al. |
| 2020/0206035 A1 | 7/2020 | Kantor et al. |
| 2020/0206036 A1 | 7/2020 | Robinson et al. |
| 2020/0214637 A1 | 7/2020 | Brownhill et al. |
| 2020/0214897 A1 | 7/2020 | Long et al. |
| 2020/0214898 A1 | 7/2020 | Waite et al. |
| 2020/0214899 A1 | 7/2020 | Locke et al. |
| 2020/0215220 A1 | 7/2020 | Schomburg et al. |
| 2020/0215226 A1 | 7/2020 | Kitagawa et al. |
| 2020/0222469 A1 | 7/2020 | Cotton |
| 2020/0229983 A1 | 7/2020 | Robinson et al. |
| 2020/0230283 A1 | 7/2020 | Yang et al. |
| 2020/0237562 A1 | 7/2020 | Rice et al. |
| 2020/0237564 A1 | 7/2020 | Hammond et al. |
| 2020/0237816 A1 | 7/2020 | Lait |
| 2020/0246195 A1 | 8/2020 | Robinson et al. |
| 2020/0253785 A1 | 8/2020 | Bernet et al. |
| 2020/0253786 A1 | 8/2020 | Harrison et al. |
| 2020/0254139 A1 | 8/2020 | Phillips et al. |
| 2020/0261275 A1 | 8/2020 | Manwaring et al. |
| 2020/0261276 A1 | 8/2020 | Lujan Hernandez et al. |
| 2020/0268560 A1 | 8/2020 | Harrison et al. |
| 2020/0268561 A1 | 8/2020 | Locke et al. |
| 2020/0270484 A1 | 8/2020 | Lipscomb et al. |
| 2020/0276055 A1 | 9/2020 | Randolph et al. |
| 2020/0276058 A1 | 9/2020 | Locke et al. |
| 2020/0277450 A1 | 9/2020 | Silverstein et al. |
| 2020/0281519 A1 | 9/2020 | Gowans et al. |
| 2020/0281529 A1 | 9/2020 | Grubb et al. |
| 2020/0281678 A1 | 9/2020 | Long et al. |
| 2020/0281775 A1 | 9/2020 | Kushnir et al. |
| 2020/0282100 A1 | 9/2020 | Gil et al. |
| 2020/0282114 A1 | 9/2020 | Long et al. |
| 2020/0282115 A1 | 9/2020 | Gardner et al. |
| 2020/0289328 A1 | 9/2020 | Luckemeyer et al. |
| 2020/0289347 A1 | 9/2020 | Gowans et al. |
| 2020/0289701 A1 | 9/2020 | Hall et al. |
| 2020/0289712 A1 | 9/2020 | Jiang et al. |
| 2020/0289723 A1 | 9/2020 | Gregory et al. |
| 2020/0289726 A1 | 9/2020 | Locke et al. |
| 2020/0289727 A1 | 9/2020 | Locke |
| 2020/0289806 A1 | 9/2020 | Locke et al. |
| 2020/0297541 A1 | 9/2020 | Hartwell et al. |
| 2020/0297543 A1 | 9/2020 | Rodzewicz et al. |
| 2020/0297544 A1 | 9/2020 | Moine et al. |
| 2020/0297892 A1 | 9/2020 | Silcock |
| 2020/0297893 A1 | 9/2020 | Ericson |
| 2020/0297894 A1 | 9/2020 | Koyama et al. |
| 2020/0299865 A1 | 9/2020 | Bonnefin et al. |
| 2020/0306089 A1 | 10/2020 | Delury et al. |
| 2020/0306091 A1 | 10/2020 | Lee et al. |
| 2020/0306094 A1 | 10/2020 | Kushnir et al. |
| 2020/0315853 A1 | 10/2020 | Waite |
| 2020/0315854 A1 | 10/2020 | Simmons et al. |
| 2020/0316271 A1 | 10/2020 | Lin |
| 2020/0323692 A1 | 10/2020 | Locke et al. |
| 2020/0324015 A1 | 10/2020 | Kettel et al. |
| 2020/0330283 A1 | 10/2020 | Locke et al. |
| 2020/0330284 A1 | 10/2020 | Locke et al. |
| 2020/0330285 A1 | 10/2020 | Rehbein et al. |
| 2020/0330658 A1 | 10/2020 | Fujisaki |
| 2020/0330660 A1 | 10/2020 | Patel et al. |
| 2020/0337719 A1 | 10/2020 | Ingram et al. |
| 2020/0337904 A1 | 10/2020 | Waite |
| 2020/0337905 A1 | 10/2020 | Earl et al. |
| 2020/0337906 A1 | 10/2020 | Long et al. |
| 2020/0337908 A1 | 10/2020 | Long et al. |
| 2020/0338228 A1 | 10/2020 | Kharkar et al. |
| 2020/0338243 A1 | 10/2020 | Harrison et al. |

FOREIGN PATENT DOCUMENTS

| | | |
|---|---|---|
| EP | 3643330 A1 | 4/2020 |
| EP | 3643331 A1 | 4/2020 |
| EP | 3669838 A1 | 6/2020 |
| EP | 3669843 A1 | 6/2020 |
| EP | 3669844 A1 | 6/2020 |
| GB | 2579211 A | 6/2020 |
| GB | 2579368 A | 6/2020 |
| WO | 2005018543 A2 | 3/2005 |
| WO | 2011121394 A1 | 10/2011 |
| WO | 2011135284 A1 | 11/2011 |
| WO | 2011144888 A1 | 11/2011 |
| WO | 2013015827 A2 | 1/2013 |
| WO | 2013126049 A1 | 8/2013 |
| WO | 2014014842 A1 | 1/2014 |
| WO | 2015145117 A1 | 10/2015 |
| WO | 2015173546 A1 | 11/2015 |

(56) References Cited

FOREIGN PATENT DOCUMENTS

| | | |
|---|---|---|
| WO | 2016141450 A1 | 9/2016 |
| WO | 2017016974 A1 | 2/2017 |
| WO | 2017125250 A1 | 7/2017 |
| WO | 2018029231 A1 | 2/2018 |
| WO | 2018094061 A1 | 5/2018 |
| WO | 2018162613 A1 | 9/2018 |
| WO | 2018163093 A1 | 9/2018 |
| WO | 2018189265 A1 | 10/2018 |
| WO | 2018226667 A1 | 12/2018 |
| WO | 2018227144 A1 | 12/2018 |
| WO | 2018231825 A1 | 12/2018 |
| WO | 2018236648 A1 | 12/2018 |
| WO | 2019002085 A1 | 1/2019 |
| WO | 2019012068 A1 | 1/2019 |
| WO | 2019012069 A1 | 1/2019 |
| WO | 2019022493 A1 | 1/2019 |
| WO | 2019027933 A1 | 2/2019 |
| WO | 2019038548 A1 | 2/2019 |
| WO | 2019038549 A1 | 2/2019 |
| WO | 2019040656 A1 | 2/2019 |
| WO | 2019050855 A1 | 3/2019 |
| WO | 2019058373 A1 | 3/2019 |
| WO | 2019073326 A1 | 4/2019 |
| WO | 2019083563 A1 | 5/2019 |
| WO | 2019083868 A1 | 5/2019 |
| WO | 2019086911 A1 | 5/2019 |
| WO | 2019091150 A1 | 5/2019 |
| WO | 2019094147 A1 | 5/2019 |
| WO | 2019096828 A1 | 5/2019 |
| WO | 2019113275 A1 | 6/2019 |
| WO | 2019113623 A1 | 6/2019 |
| WO | 2019191590 A1 | 10/2019 |
| WO | 2019193141 A1 | 10/2019 |
| WO | 2019193333 A1 | 10/2019 |
| WO | 2019199389 A1 | 10/2019 |
| WO | 2019199596 A1 | 10/2019 |
| WO | 2019199687 A1 | 10/2019 |
| WO | 2019199798 A1 | 10/2019 |
| WO | 2019199849 A1 | 10/2019 |
| WO | 2019200035 A1 | 10/2019 |
| WO | 2019215572 A1 | 11/2019 |
| WO | 2019219613 A1 | 11/2019 |
| WO | 2019234365 A1 | 12/2019 |
| WO | 2020005062 A1 | 1/2020 |
| WO | 2020005344 A1 | 1/2020 |
| WO | 2020005536 A1 | 1/2020 |
| WO | 2020005546 A1 | 1/2020 |
| WO | 2020005577 A1 | 1/2020 |
| WO | 2020007429 A1 | 1/2020 |
| WO | 2020011691 A1 | 1/2020 |
| WO | 2020014178 A1 | 1/2020 |
| WO | 2020014310 A1 | 1/2020 |
| WO | 2020018300 A1 | 1/2020 |
| WO | 2020026061 A1 | 2/2020 |
| WO | 2020026144 A1 | 2/2020 |
| WO | 2020033351 A1 | 2/2020 |
| WO | 2020035811 A1 | 2/2020 |
| WO | 2020043665 A1 | 3/2020 |
| WO | 2020044237 A1 | 3/2020 |
| WO | 2020046443 A1 | 3/2020 |
| WO | 2020047255 A1 | 3/2020 |
| WO | 2020049038 A1 | 3/2020 |
| WO | 2020055945 A1 | 3/2020 |
| WO | 2020056014 A1 | 3/2020 |
| WO | 2020056182 A1 | 3/2020 |
| WO | 2020065531 A1 | 4/2020 |
| WO | 2020070231 A1 | 4/2020 |
| WO | 2020074512 A1 | 4/2020 |
| WO | 2020078993 A1 | 4/2020 |
| WO | 2020079009 A1 | 4/2020 |
| WO | 2020079330 A1 | 4/2020 |
| WO | 2020081259 A1 | 4/2020 |
| WO | 2020081391 A1 | 4/2020 |
| WO | 2020092598 A1 | 5/2020 |
| WO | 2020136555 A1 | 7/2020 |
| WO | 2020141059 A1 | 7/2020 |
| WO | 2020144347 A1 | 7/2020 |
| WO | 2020150548 A1 | 7/2020 |
| WO | 2020159675 A1 | 8/2020 |
| WO | 2020159892 A1 | 8/2020 |

\* cited by examiner

PERFORATED BINDER FOR LAMINATED WOUND DRESSING

CROSS-REFERENCE

This Application is a continuation application of U.S. patent application Ser. No. 13/689,133, filed Nov. 29, 2012, which claims priority to U.S. Provisional Patent Application No. 61/564,612, filed Nov. 29, 2011, each of which is incorporated in its entirety by reference herein.

STATEMENT REGARDING FEDERALLY SPONSORED RESEARCH OR DEVELOPMENT

Not Applicable

BACKGROUND OF THE INVENTION

Field of Invention

The present invention relates generally to wound dressings and particularly to a process of fabricating a perforated binder for a laminated dressing.

Description of the Related Art

Dressings have long been known in the art for protecting and treating wounds or areas of the epidermis that display irritation or visible infection. (Hereinafter, "wounds" is understood to encompass a wide variety of skin injuries and irregularities, including lacerations and puncture wounds as well as, e.g., rashes and eczema.) In recent decades, medical practitioners have come to understand the benefits of including an antimicrobial or anti-infection agent in the dressing to prevent infection of the wound during treatment.

Scarring is a natural part of the healing process. Scar tissue consists mainly of protein collagen formed during the skin's process of wound repair. With the exception of very minor lesions, skin wounds following accidents, disease or surgery all result in some degree of visible scarring. Where the scar tissue is large or in a prominent position on the body, it can be readily apparent to a casual observer and embarrassing or otherwise troubling for the scarred person. It is therefore desirable to have a wound dressing that can help minimize the appearance of scarring during the healing process.

An open wound is at a heightened risk of infection throughout the healing process. In particular, microorganisms such as bacteria and fungi will attempt to establish themselves in the moisture of the exudate extruded from the wound during the healing process. Medical practitioners have discovered that certain metals and metallic compounds, and in particular silver ions, when delivered to a wound, can kill microorganisms within and on the surface of the wound and thereby help fight infection.

It is therefore desirable to have a wound dressing that can supply an antimicrobial agent, such as silver ions, to a wound while also helping the wound to heal in a way to reduce the appearance of scar tissue.

BRIEF SUMMARY OF THE INVENTION

The present invention in some of its embodiments is directed toward a laminated dressing comprising three layers: a lower layer, comprising a fiber material, to directly contact a patient's skin and a wound area; an upper layer, comprising a foam or foam-like material to absorb exudate and moisture; and a middle layer or binder layer, comprising a binder material to bind the fiber-based lower layer and the foam-based upper layer. When the dressing is applied to a patient's skin and wound, the fiber-based lower layer is placed in direct contact with the patient's skin, generally covering the wound at least in part; the binder layer and foam-based upper layer sit on top of the fiber-based lower layer with respect to the patient's skin. Generally, during the manufacture or fabrication of a multi-layer or laminated dressing, the layers are brought together and heated in order to promote the formation of bonds—including, in various embodiments and depending on the materials used, physical and chemical bonds—between the multiple layers. The binder layer generally comprises a polymer-based fiber, such as a polyester or polyamide fiber, or a blend of such materials. Often, during the heating process, a polymer-based binder layer melts; when the melted binder layer re-solidifies at a later stage, the resulting binder layer is largely moisture-impermeable and therefore inhibits the transmigration of exudate or other moisture from the lower layer to the upper layer. The melting of the binder layer during the fabrication process results in a binder layer that inhibits the proper function of the laminated dressing, which aims to allow the foam-based upper layer draw moisture and exudate away from the wound and the lower layer in order to keep the wound dry and inhibit infection and irritation.

One way to limit the undesired results of the melting of the binder layer during the fabrication process is to cut perforations or holes in the binder layer before the binder layer is positioned between the lower layer and the upper layer. The pre-cut perforations ensure that, when the binder layer has melted, and then re-solidified after cooling, the re-solidified binder layer still includes perforations, through which moisture and exudate may pass from the lower layer to the upper layer.

However, when cutting perforations in a sheet of material for a binder layer, it is necessary to ensure that the cut-out material from the binder layer physically separates from the binder layer before the binder layer is positioned between the lower layer and the upper layer. In some example embodiments of the present general inventive concept, cut-out material from the binder layer is physically separated from the binder layer by adhering the cut-out material to a sheet covered with an adhesive material, such as a glue material. A binder layer is brought into contact with a sheet coated with a pattern of adhesive material (a "pattern-coated adhesive sheet"). As the binder layer is in contact with the pattern-coated adhesive sheet, a series of closed-loop cuts are made in the binder layer. The closed-loop cuts are made in such a way that the material enclosed by each closed loop is substantially physically separated from the remainder of the binder layer. Then the binder layer is moved away from the pattern-coated adhesive sheet, so that the binder layer and the pattern-coated adhesive sheet are no longer in contact. When the binder layer and the pattern-coated adhesive sheet are moved apart, the material enclosed in the closed-loop cuts—i.e., the cut waste fragments—are retained on the pattern-coated adhesive sheet, ensuring that the binder layer includes a series of cleared perforations.

In some embodiments of the present general inventive concept, a laminated dressing comprises a lower layer, comprising a fiber material, to directly contact a patient's skin and a wound area; an upper layer, comprising a foam or foam-like material to absorb exudate and moisture; and a binder layer, comprising a binder material to bind the fiber-based lower layer and the foam-based upper layer, the binder layer including a series of perforations. In some embodiments, said lower layer is fabricated from a nonwoven, spunlaced polymer fabric. In some embodiments, said lower layer is fabricated from polyethylene fibers. In some embodiments, at least some of said polyethylene fibers are coated with silicone. In some embodiments, said lower layer is fabricated from regenerated cellulose fiber material. In some embodiments, some of said regenerated cellulose fiber material includes silicone. In some embodiments, said upper layer is fabricated from polyurethane. In some embodiments, said upper layer includes an antimicrobial agent. In some embodiments, said antimicrobial agent is inorganic. In some embodiments, said antimicrobial agent is metal-based. In some embodiments, said binder layer is fabricated from a polyester or polyamide material.

In some embodiments of the present general inventive concept, a method of fabricating a binder layer for a laminated dressing comprises bringing a binder layer into contact with a pattern-coated adhesive sheet; making a series of closed-loop cuts in the binder layer; and moving the binder layer away from the pattern-coated adhesive sheet, such that the binder layer and the pattern-coated adhesive sheet are no longer in contact, such that the material enclosed in the closed-loop cuts is retained on the pattern-coated adhesive sheet, whereby the binder layer includes a series of cleared perforations.

BRIEF DESCRIPTION OF THE SEVERAL VIEWS OF THE DRAWINGS

The above-mentioned and additional features of the invention will become more clearly understood from the following detailed description of the invention read together with the drawings in which.

DETAILED DESCRIPTION OF THE INVENTION

The present invention in some of its embodiments is directed toward a process of fabricating a perforated binder for a laminated dressing.

According to one embodiment of the present general inventive concept, illustrated generally at FIG. 1, a laminated dressing 10 comprises three layers: a lower layer 20, comprising a fiber material, to directly contact a patient's skin and a wound area; an upper layer 30, comprising a foam or foam-like material to absorb exudate and moisture; and a middle layer or binder layer 40 (hereinafter "binder layer"), comprising a binder material to bind the fiber-based lower layer 20 and the foam-based upper layer 30. When the dressing 10 is applied to a patient's skin and wound, the fiber-based lower layer 20 is placed in direct contact with the patient's skin, generally covering the wound at least in part; the binder layer 40 and foam-based upper layer 30 sit on top of the fiber-based lower layer 20 with respect to the patient's skin.

Figure 1:
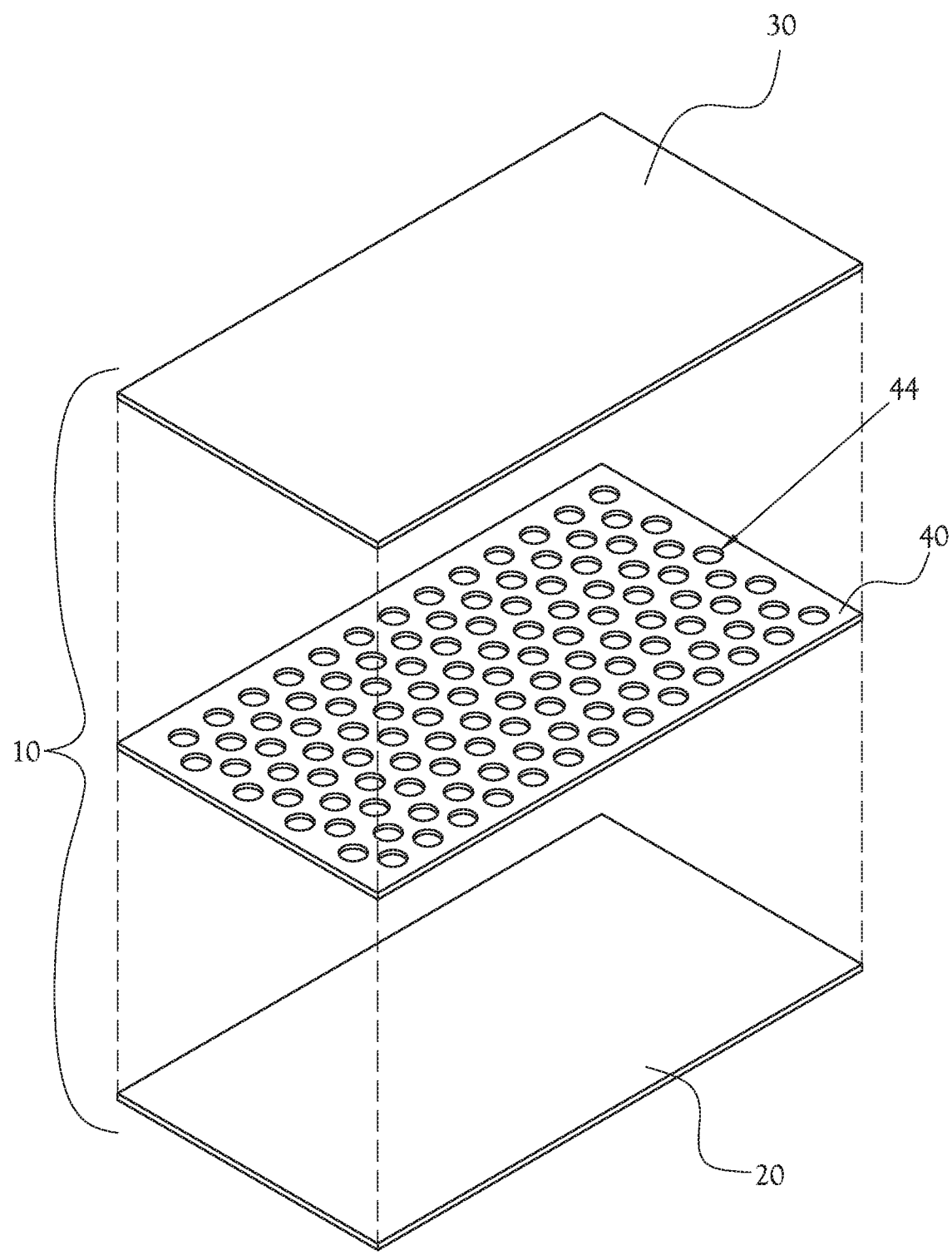
FIG. 1 is an exploded view of an example embodiment of the present invention.

Generally, during the manufacture or fabrication of a multi-layer or laminated dressing like the example embodiment dressing 10 illustrated in FIG. 1, the layers are brought together and heated in order to promote the formation of bonds—including, in various embodiments and depending on the materials used, physical and chemical bonds—between the multiple layers. The binder layer 40 generally comprises a polymer-based fiber, such as a polyester or polyamide fiber, or a blend of such materials. Often, during the heating process, a polymer-based binder layer 40 melts; when the melted binder layer 40 re-solidifies at a later stage, the resulting binder layer 40 is largely moisture-impermeable and therefore inhibits the transmigration of exudate or other moisture from the lower layer 20 to the upper layer 40. The melting of the binder layer 40 during the fabrication process results in a binder layer 40 that inhibits the proper function of the laminated dressing 10, which aims to allow the foam-based upper layer 30 draw moisture and exudate away from the wound and the lower layer 20 in order to keep the wound dry and inhibit infection and irritation.

One way to limit the counterproductive results of the melting of the binder layer 40 during the fabrication process is to cut perforations or holes 44 in the binder layer 40 before [[it]] the binder layer 40 is positioned between the lower layer 20 and the upper layer 30. Thus, for example, in the exploded view of an illustrated example embodiment, shown in FIG. 1, the binder layer 40 includes numerous perforations 44. The pre-cut perforations 44 (pre-cut in so far as the excised material is removed from the binder layer 40 before said binder layer 40 is inserted between the lower layer 20 and the upper layer 30) ensure that, when the binder layer 40 has melted, and then re-solidified after cooling, the re-solidified binder layer 40 still includes perforations, through which moisture and exudate may pass from the lower layer 20 to the upper layer 30.

Figure 2A:
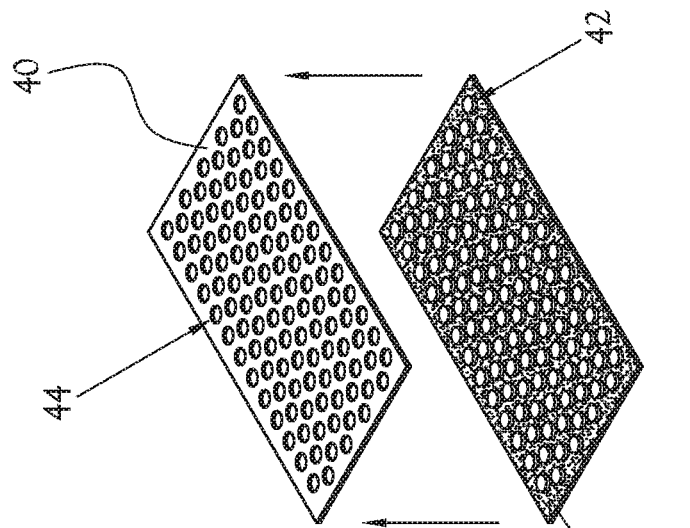
FIG. 2A is a view of one stage of one embodiment of a process for removing cut material from a binder layer to form a perforated binder layer, showing an unperforated binder layer and a pattern-coated adhesive sheet.
Figure 2B:
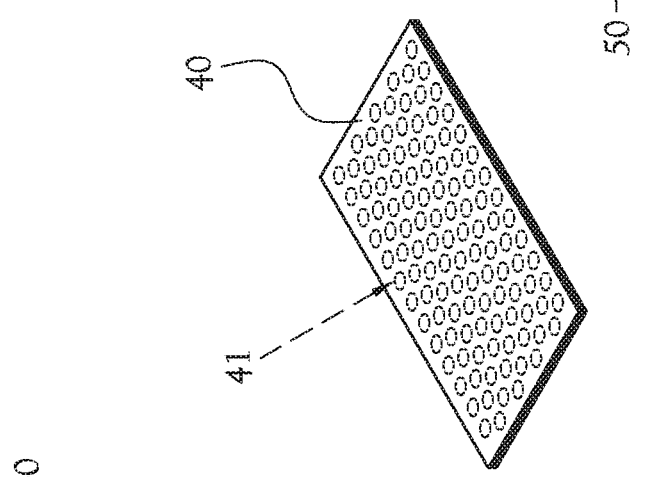
FIG. 2B is a view of another stage of the example embodiment process shown in FIG. 2A, showing the binder layer in contact with the pattern-coated adhesive sheet.
Figure 2C:
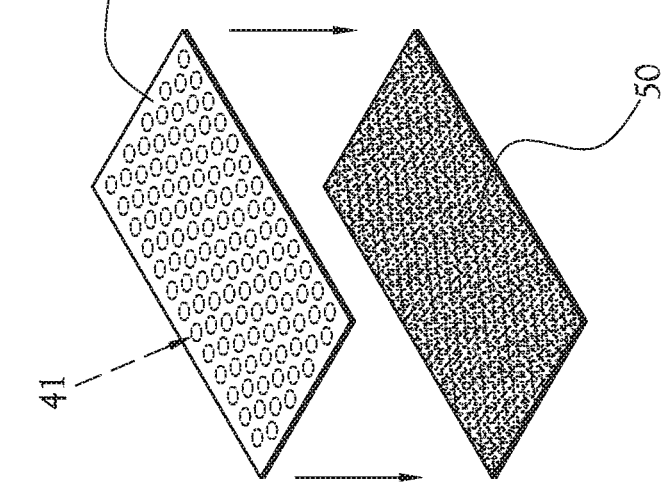
FIG. 2C is a view of another stage of the example embodiment process shown in FIGS. 2A and 2B, showing the now-perforated binder layer moved away from the pattern-coated adhesive sheet.

However, when cutting holes 44 in a sheet of material for a binder layer, it is necessary to ensure that the cut-out material from the binder layer 40 physically separates from the binder layer 40 before the binder layer 40 is positioned between the lower layer 20 to the upper layer 30. In some example embodiments of the present general inventive concept, cut-out material from the binder layer 40 is physically separated from the binder layer 40 by adhering the cut-out material to a sheet covered with an adhesive material, such as a glue material. One example embodiment of a process according to one aspect of the present general inventive concept is illustrated generally in FIGS. 2A through 2C. In FIG. 2A, a binder layer 40 is brought into contact with a sheet 50 coated with a pattern of adhesive material (hereinafter, "pattern-coated adhesive sheet"). In FIG. 2B, the binder layer 40 is shown in contact with the pattern-coated adhesive sheet 50, with one face of the binder layer 40 substantially pressed against one face of the pattern-coated adhesive sheet 50. As the binder layer 40 is in contact with the pattern-coated adhesive sheet 50, a series of closed-loop cuts are made in the binder layer 40, generally along the phantom lines 41 shown on the binder layer 40 in FIGS. 2A and 2B. The closed-loop cuts are made in such a way that the material enclosed by each closed loop is substantially physically separated from the remainder of the binder layer 40. In FIG. 2C, the binder layer 40 is moved away from the pattern-coated adhesive sheet 50, so that the binder layer 40 and the pattern-coated adhesive sheet 50 are no longer in contact. When the binder layer 40 and the pattern-coated adhesive sheet 50 are moved apart, the material enclosed in the closed-loop cuts—i.e., the cut waste fragments 42—are retained on the pattern-coated adhesive sheet, ensuring that the binder layer 40 includes a series of cleared perforations 44.

Figure 3:
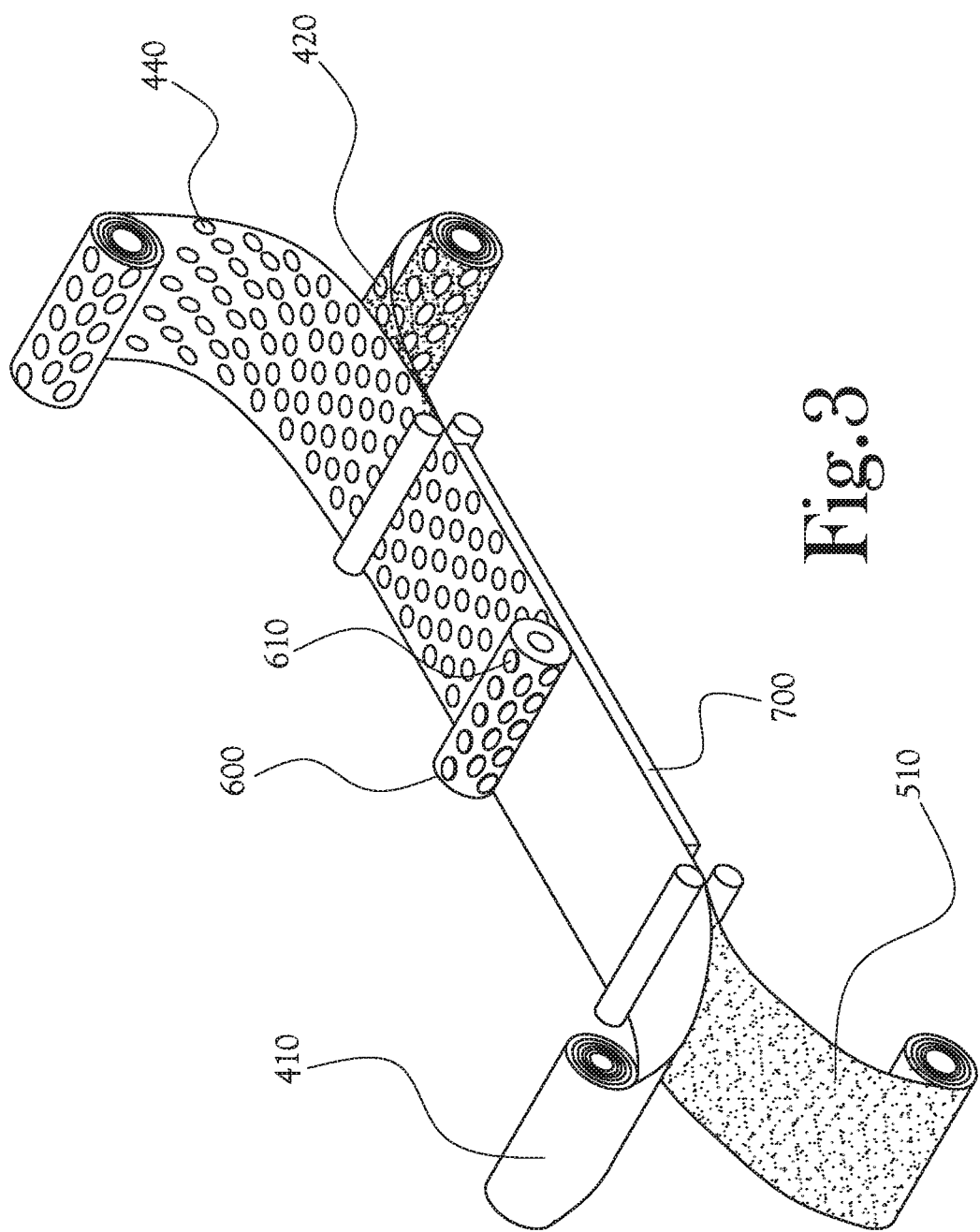
FIG. 3 is a perspective view of one embodiment of a process for form a perforated binder layer.

FIG. 3 illustrates one embodiment of a process for fabricating a perforated binder layer according to the present general inventive concept. In the illustrated example embodiment, a roll of binder layer 410 is unspooled and brought into contact with a roll of pattern-coated adhesive sheet 510, and the two rolls in contact are moved onto an assembly line 700. On the assembly line 700, a rolling cutter 600 is positioned above the roll of binder layer 410. The rolling cutter 600 includes a series of cutting punches 610, which make closed-loop cuts in the roll of binder layer 410. Then the binder layer 410 is moved away from the pattern-coated adhesive sheet 510, so that the binder layer 410 and the pattern-coated adhesive sheet 510 are no longer in contact. When the binder layer 410 and the pattern-coated adhesive sheet 510 are moved apart, the material enclosed in the closed-loop cuts—i.e., the cut waste fragments 420—are retained on the roll of pattern-coated adhesive sheet 510, ensuring that the binder layer 410 includes a series of cleared perforations 440.

In some embodiments, the lower layer comprises polyethylene fibers. In some embodiments, the lower layer comprises a porous mesh of polyethylene fibers. In some embodiments, the lower layer comprises a spun regenerated fiber material. In some embodiments, some or all of the fibers are coated with silicone. In some embodiments, the fibers are not coated with silicone.

In some embodiments, the foam-based upper layer comprises a foam fabricated from a hydrophilic polyurethane or comparable material. In some embodiments, the foam-based upper layer includes a metal-based antimicrobial agent that undergoes a controlled release when the binder layer comes into contact with moisture. In some embodiments, the upper layer includes an inorganic antimicrobial agent. In some embodiments, the upper layer does not include an inorganic antimicrobial agent.

When the dressing is used, the lower layer is applied directly to a patient's skin, covering or substantially covering the wound. The silicone in the lower layer interacts with the wound to minimize the appearance of scar tissue.

The dressing is either pre-wetted or applied dry to the wound. Moisture, either applied beforehand or from the wound exudate, travels through the porous fiber-based lower layer, through the binder layer, into the foam upper layer.

In some embodiments, moisture acts to release metal ions from controlled-release mechanisms, such as zeolites containing the metal ions, in the foam-based upper layer. The ions then travel within the moisture into the wound, where they act to kill bacteria and other infectious microorganisms and to prevent infections from gaining a foothold.

While the present invention has been illustrated by description of several embodiments and while the illustrative embodiments have been described in considerable detail, it is not the intention of the applicant to restrict or in any way limit the scope of the appended claims to such detail. Additional advantages and modifications will readily appear to those skilled in the art. The invention in its broader aspects is therefore not limited to the specific details, representative apparatus and methods, and illustrative examples shown and described. Accordingly, departures may be made from such details without departing from the spirit or scope of applicant's general inventive concept.

What is claimed is:

1. A method of fabricating a laminated dressing comprising:
   bringing a binder layer into contact with a pattern-coated adhesive sheet;
   making a series of closed-loop cuts in the binder layer; and
   moving the binder layer away from the pattern-coated adhesive sheet, such that the binder layer and the pattern-coated adhesive sheet are no longer in contact, such that a material enclosed in the closed-loop cuts is retained on the pattern-coated adhesive sheet, whereby the binder layer includes a series of cleared perforations.

2. The method of claim 1 wherein said binder layer is fabricated from a polyester or polyamide material.

3. The method of claim 1, further comprising positioning the binder layer between a lower layer and an upper layer.

4. The method of claim 3, wherein the lower layer comprises a fiber material configured to directly contact a patient's skin and a wound area.

5. The method of claim 3, wherein the upper layer comprises a foam material configured to absorb exudate and moisture.

6. The method of claim 3, wherein the lower layer comprises a fiber material configured to directly contact a patient's skin and a wound area and the upper layer comprises a foam material configured to absorb exudate and moisture.

7. The method of claim 3, further comprising forming the lower layer from a non-woven, spunlaced polymer fabric.

8. The method of claim 3, further comprising forming the lower layer from polyethylene fibers.

9. The method of claim 8, further comprising coating at least some of the polyethylene fibers with silicone.

10. The method of claim 3, further comprising forming the lower layer from regenerated cellulose fiber material.

11. The method of claim 10, further comprising including silicone in at least some of the regenerated cellulose fiber material.

12. The method of claim 3, wherein said upper layer is fabricated from polyurethane.

13. The method of claim 3, further comprising including an antimicrobial agent in the upper layer.

14. The method of claim 13, wherein the antimicrobial agent is inorganic.

15. The method of claim 13 wherein said antimicrobial agent is metal-based.

\* \* \* \* \*